United States Patent [19]

Smith

[11] Patent Number: 5,490,849
[45] Date of Patent: Feb. 13, 1996

[54] UNIFORM-RADIATION CAUSTIC SURFACE FOR PHOTOABLATION

[76] Inventor: Robert F. Smith, 3714 Henley Dr., Pittsburgh, Pa. 15235

[21] Appl. No.: 824,775

[22] Filed: Jan. 23, 1992

Related U.S. Application Data

[63] Continuation-in-part of Ser. No. 552,298, Jul. 13, 1990, abandoned.

[51] Int. Cl.⁶ ........................................ A61M 5/06
[52] U.S. Cl. ........................ 606/5; 606/3; 606/13; 606/17; 606/18; 219/121.6; 219/121.74; 219/121.75; 219/121.77; 219/121.83
[58] Field of Search ..................... 128/393, 397, 128/398; 606/2–19; 219/121.6, 121.67, 121.73–121.77, 121.85

[56] References Cited

U.S. PATENT DOCUMENTS 4,724,522  2/1988  Belgorod ........................ 606/5
4,887,592  12/1989  Loertscher ..................... 606/5
5,102,409  4/1992  Balgorod ....................... 606/5
5,141,506  8/1992  York ............................. 606/3

*Primary Examiner*—David M. Shay

[57] ABSTRACT

A simultaneously generated caustic surface comprised of high energy photons is created for the purpose of ablating organic materials to within optical accuracies. The apparatus and method are principally for modifying, in vivo, the anterior cornea of the eye to effect refractive correction thereof. A catadioptric system in tandem with a continuously adjustable system of lenses provides a range of spherical or aspherical caustic curvatures throughout which range relatively uniform radiation intensity is maintained over the entire caustic. Ablation monitoring uses both visual and interferometric means; control is performed using interferometry in conjunction with a computer controlled excimer laser.

24 Claims, 14 Drawing Sheets

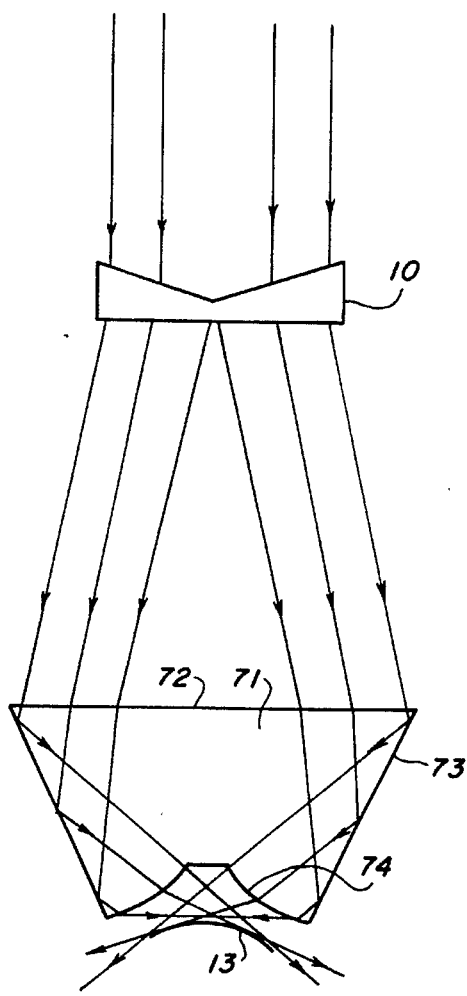
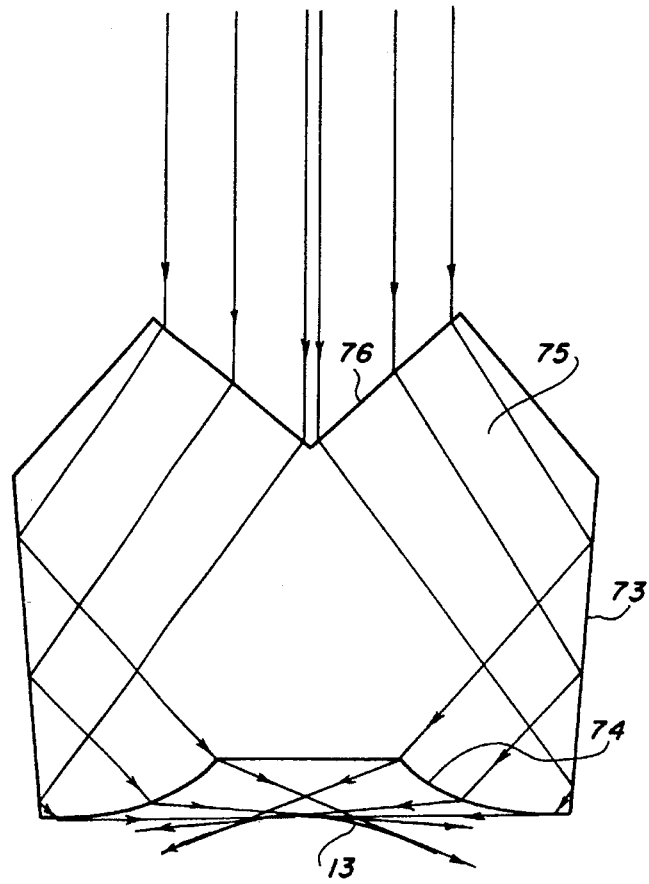
FIG. 7
FIG. 8

UNIFORM-RADIATION CAUSTIC SURFACE FOR PHOTOABLATION

CROSS REFERENCE TO RELATED APPLICATIONS

This application is a continuation-in-part of U.S. patent application Ser. No. 07/552,298, filed Jul. 13, 1990, abandoned.

BACKGROUND OF THE INVENTION

This invention relates to an apparatus and method, generally for optical milling/shaping/reprofiling of solid organic materials, and specifically for reshaping the anterior surface of the cornea of the human eye for the purpose of correcting refractive defects.

Recent investigations have demonstrated the property of high energy photon radiation in the ultraviolet, such as is generated by the argon fluoride excimer laser (AFEL), to break the intermolecular bonds of organic materials—in effect disintegrating/ablating molecules exposed to this radiation while leaving the adjacent unexposed molecular structure intact resulting in an optically smooth interface. Because existing precision molding and optical lathing techniques can rapidly and accurately produce plastic optics, production of these using the AFEL does not, as yet, offer a superior means of manufacture. However, application of AFEL to living corneal tissue does offer a means for optically accurate corneal surface reshaping not achievable by other means, and with minimal diminution in transparency and trauma to adjacent interface cells. This characteristic has led to the application of the AFEL to corneal surgery including the refractive altering procedures of radial keratotomy, keratomileusis (corneal keratectomy), and anterior corneal surface modification (photorefractive keratectomy), the latter having greater potential for achieving optical accuracy and predictability than the preceding methods.

Existing methods being applied in photorefractive keratectomy involve the use of the scanning slit-beam lasers and constricting diaphragm controlled beams such as are described in U.S. Pat. Nos. 4,729,372, 4,770,172, 4,903,695, 4,941,093, 4,732,148. These inventions all use an en face method, that is, they direct a collimated laser beam collinear with the axis of the eye head-on onto the cornea. Concern over such direct radiation entering the eye is addressed in U.S. Pat. No. 4,840,175 by first removing a corneal slice (lamellar keratectomy) and ablating this slice in vitro. Another means for avoiding direct radiation into the eye is found in U.S. Pat. No. 4,724,522 by Belgorod which proposes a tangentially directed laser beam formed by mirrors mechanically rotating about the axis of the cornea to lathe the corneal surface; such a one or two dimensional technique is hampered by its extreme aiming accuracy requirements and being very time consuming in its application.

It is an object of the present invention to reduce the possible trauma associated with en face corneal ablation by use of a tangential means which avoids the problems of being highly sensitive and time consuming inherent in rotating-optical and/or small-spot-scanning excimer laser delivery systems.

A three dimensional tangential technique is presented in the European Patent Application 0222537 of York that avoids the two above-cited problems of the Belgorod patent, but does so at the expense of being limited by having a mirror element capable of generating only single fixed corneal shape, and further suffers from an excessive variation of radiation intensity (fluence) upon the corneal surface.

It is a further object of this invention to provide a method and apparatus incorporating a three dimensional tangential approach that allows the generation of a continuum of surface curvatures using a single optical device while at the same time providing a uniform radiation intensity over the full surface to be ablated.

Resorting to a tangential technique strictly because of a concern AFEL radiation could enter the eye and do damage to the inner eye, is unfounded as can be demonstrated by application of Beer's law, which states that light transmission varies as the power of ten raised to the negative product of the absorbance and the depth of penetration. At a wavelength of 193 nanometers (nm), 90% of the energy is absorbed in the first 10 microns (um) of corneal surface depth, and at the posterior surface of a cornea of normal thickness, approximately ten to the minus 60th power of the surface energy exists. Furthermore, much photo-ablative refractive surgery has already been performed without revealing any such damage. However, this fact alone does not imply that there are no differences between en face and tangential methods; the high energy AFEL pulses give rise to phonon shock waves, which if severe enough can damage the endothelium of the cornea or other eye structures. It can be reasoned that such undesired effects would be reduced by the glancing action of tangential radiation compared to the direct impact of en face radiation. Of even greater significance is the property of tangential radiation to cease ablating beyond a certain point which contrasts with en face radiation—i.e., the extent of tangential ablation for a given radiation intensity is distance dependent and hence self limiting, whereas the en face method is time dependent only. Essentially, it is this difference from en face methods that the present invention uses to enable the ablation of a distorted anterior cornea surface, having either regular or irregular astigmatism, to produce a corneal surface matching the smoothness and uniformity of that of the emmetropic human eye.

The cited patents of York and Belgorod both imply that the final shape imparted to the cornea matches that of the three dimensional locus of points tangential to a surface of desired curvature, referred to as a caustic. In truth, the actual surface ultimately imparted to the cornea is defined not by this caustic, but by a surface of shallower curvature, displaced from the caustic, and defined as the three dimensional locus of points where the rays intersect this new curvature at a constant, non-zero angle. The value of this angle, called a grazing angle, corresponds to the angle where the absorption of radiation energy into the cornea or ablatable material just rises above the ablation threshold of the particular material, the remainder of radiation being reflected away from the surface. Because the value of the grazing angle and radiation intensity are inversely related, ablation depth varies with intensity; thus to insure that the ablated surface curvature differs from the caustic curvature by a constant value, radiation intensity should be maintained substantially uniform.

That the York patent results in intensity variations amounting to orders of magnitude across the cornea surface area typically ablated, can be qualitatively demonstrated as follows: Beginning with York's collimated laser beam having an annular cross section of uniform intensity, this annular beam is intercepted by an annular mirror and is reflected in such a way as to form a dome of intersecting rays (i.e. a caustic) that impinge upon the cornea. Next, two equal width concentric bands on the mirror are considered: The first is a band around the periphery of the mirror, the second is a band around the center hole of the mirror. Energy reflected within the first band impinges on the cornea in the shape of a circle centered on the axis of the cornea having a radius r. Energy from the second band is reflected to the periphery of the cornea at a distance R from the axis, producing a band of approximate width r. Then, since the energy E is approximately equal in both bands, the intensity of radiation due to the first band is $I_1=E/\pi r^2$, while the second band causes an energy intensity on the cornea of $I_2=E/2\pi Rr$, giving the ratio $I_1/I_2=2R/r$. Although these formulas are approximate, they illustrate the fact that York's method causes the radiation intensity upon the cornea to vary inversely with the radial distance from the axis. For example, the variation between the intensity within a 0.25 mm radius around the corneal axis is higher than the intensity at a peripheral distance of 4 mm by more than a factor of 30. Further, the fact that York claims only a single reflecting precludes any means for eliminating the inherent non-uniformity because the desired shape of the cornea uniquely dictates the shape of the mirror leaving no additional degree of freedom to impose a constraint to simultaneously achieve uniform intensity.

Further, in York's method, to insure that radiation intensity rises above the threshold value of ablation in the peripheral region of the cornea, the radiation intensity near the axis of the cornea must rise to values in excess of 1 joule/cm$^2$. Such high intensities have been associated with thermal effects on corneal tissue, and consequently can result in damage to adjacent tissue, thus defeating the intended effect of excimer laser photoablation. (See for example, Aron-Rosa, et.al. "Keratorefractive Surgery with the Excimer Laser" Am. Journal Opht. Nov. 1985, pp 741–742.)

Therefore, it is a principal object of this invention to reduce or eliminate intensity variations, such as occur in the York patent, so as to prevent thermal damage and insure that the full corneal surface is subjected to substantially uniform intensity radiation of an optimum value.

Inherent in the patent of York, is the necessity that a significant portion of the laser beam be masked off to produce the required annular beam cross section. Because the caustic surfaces needed for corneal ablation are on the order of one square centimeter or more, present excimer laser technology is limited to about the radiation intensity mandated for such an area, and therefore any inefficiencies can be detrimental.

So, it is also an object of this invention to utilize the available laser beam with maximum efficiency.

An essential optical element of this invention is a specialized conical lens called an axicon which in conjunction with a specialized mirror forms a catadioptric system which achieves the object of the invention relating to uniformity of radiation intensity. In the patent of Marshall, et.al. (U.S. Pat. No. 4,941,093) use is made of axicon lenses to produce continuously variable size annular beams for en face photoablation. However, the intensity within the annulus is not uniform making the successful application of an axicon or combination of axicons for photoablation, somewhat dubious. In the present invention, the application of an axicon is totally difference from the Marshall patent; this is not only because the tangential method rather than the en face method is being used here, but much more importantly, it is because the intensity non-uniformity of the axicon, in combination with the complementary intensity non-uniformity of the mirror of the present invention, creates the sought-after caustic of uniform intensity.

In addition to the refractive errors of myopia, hyperopia, and astigmatism, the inability of the eye to change its focus or accommodate, known as presbyopia, is an unavoidable problem that afflicts all humans past middle age. Recent work in the field of refractive aspheric and diffraction contact or interocular lenses has shown promise in the amelioration or correction of this visual problem.

It is a further object of this invention to provide a method and apparatus that will enable corneas to be ablated throughout a continuum of aspherical curvatures for the purpose of optimizing visual acuity over as large a depth of field as possible without changing the accommodation of the lens of the eye.

SUMMARY OF THE INVENTION

It is summarily the object of this invention to provide a method and apparatus to reprofile by photoablation an ablatable material, such as the cornea of the eye to any shape, subject to ophthalmological limitations, to achieve this reprofiling by means of generating a three dimensional tangential array of rays simultaneous with each laser pulse; that this tangential array of rays, or caustic surface, possesses substantially uniform radiation intensity, that upon contacting the cornea at a minimum predetermined grazing angle cause the cornea to be ablated to a predetermined shape thereby modifying the refraction of the eye to correct for myopic, regular and/or irregular astigmatism impairment, and ameliorate the effects of presbyopia; further to accomplish this objective by a method and apparatus yielding high optical accuracy and repeatability, maximum safety, a minimum of critical adjustments, and being of relatively low complexity and cost.

According to a preferred embodiment of the present invention, a method and apparatus is given wherein a collimated source beam of photons of energy sufficient to break the molecular bonds of corneal cell tissue, such as an excimer laser, is directed into a specialized assembly of lenses called a decollimator, out of which the decollimated beam is directed into an axicon lens and mirror catadioptric system to create a caustic surface of uniform intensity, which caustic surface when advanced into the target organic material such as the cornea of the eye, photoablates said material to a predetermined optically accurate surface.

In accord with the preferred embodiment of the invention, the decollimator consists of two spherical lenses and one aspherical lens. By varying the spacing among the lenses a continuum of caustic field curvatures ranging from spherical to aspherical is produced.

A variation within the preferred embodiment of the invention involves making the aspherical mirror element spherical and replacing one of the spherical lenses with an aspherical lens to produce the same effect as the aspherical mirror.

Further according to the present invention, there is presented a means for incrementally advancing the optical device to bring the caustic field into contact with the cornea at a controllable time rate of advance.

In alternate embodiments of the invention:

(1) the axicon lens is replaced by a mirror (2) the mirror in the preferred embodiment is replaced by a lens, which utilizing total internal reflection, performs the function of the mirror in creating the caustic field (3) the axicon-mirror combination of the preferred embodiment is replaced by a single refractive structure also utilizing total internal reflection (4) the (diverging) axicon lens in the preferred embodiment is replaced by a converging axicon and the mirror in the preferred embodiment is modified to permit the cornea to protrude into the hole in the mirror Applicable to all the foregoing embodiments are advancing mechanisms which may be mechanical, electrical, pneumatic, or hydraulic or combinations thereof. Whatever type of advancing mechanism is used it is necessary to minimize any undesired movement or vibration between the optical system and a vacuum ring which holds the cornea or other ablatable material in place.

Applicable to the decollimator of the preferred embodiment is an increase in the number of lenses either spherical or aspherical for purposes of increasing the degrees of freedom in achieving all the objects of the present invention.

Monitoring of the ablation process may be facilitated by:

(1) a microscope arrangement for corneal inspection
(2) a form of corneoscope integrated into the optical system
(3) a laser radiation redirecting mirror permitting visual axial examination of the cornea
(4) an interferometer corneal surface topography, which also may be used to compensate for in vivo corneal position variations.

Necessary to the implementation of the invention is the development of a mathematical means or algorithm for generating the aspherical surfaces of the optical elements. An algorithmic procedure produces the cross sectional (meridional) coordinates of the aspheric surfaces of revolution; these coordinates are then curve fitted to a high order polynomial for use in a computer controlled optical lathing process.

BRIEF DESCRIPTION OF THE DRAWINGS

FIG. 7 shows a two lens alternate embodiment.

FIG. 8 shows a single lens alternate embodiment.

DETAILED DESCRIPTION OF THE INVENTION

Figure 1:
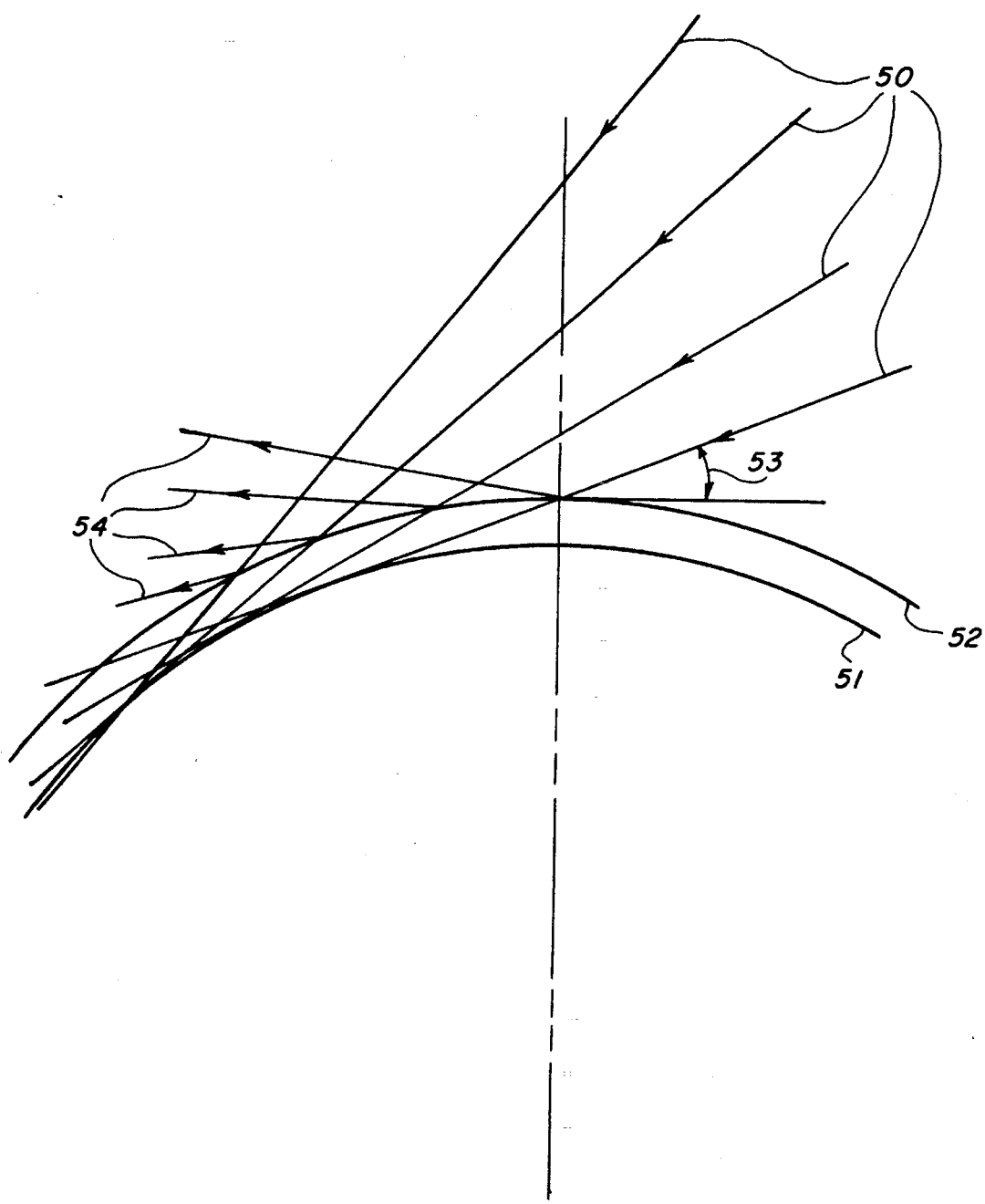
FIG. 1 depicts the physical principles relating to photoablation using tangentially directed rays.

Beginning with a basic explanation of the physical properties governing the application of this invention, FIG. 1 shows four ultraviolet light rays such as would be produced by a 193 nm excimer laser source. These rays 50 are directed so that they are tangential to a desired surface of curvature 51. The method of the invention gives rise to a continuum of rays between pairs of the four shown rays 50; the locus of points of adjacent intersecting rays forms a so-called caustic or caustic surface which is identical to the surface of curvature 51. If an ablatable material having the same curvature as the caustic, is advanced into the caustic, ablation will not begin to occur until the grazing angle 53 of the rays exceeds a certain minimum of threshold value. This threshold value is a both a function of the minimum value of radiation intensity required for the inception of ablation and the surface reflectance property of the material. In FIG. 1, surface reflectance is illustrated by the four reflected rays 54. For example, PMMA and corneal stroma both evince a threshold radiation intensity of about 50 mJ/cm$^2$; the surface reflectance of PMMA is about 50% at a grazing angle (i.e. 90°—angle of incidence) of about 8°. Therefore, if the intensity of the rays 50 is 100 mJ/cm$^2$, ablation will just begin at a grazing angle of 8°. As a consequence of these factors, the final ablated surface will be shallower than the caustic surface (i.e. have a higher radius of curvature) as illustrated by the curve 52 in FIG. 1.

Photoablatable materials are characterized not only by a threshold of radiation intensity, but also a maximum or saturation value beyond which the rate of material removed does not change. This saturation value is typically 250–300 mJ/cm$^2$ for stromal tissue. For the application of the en face method it has been shown (see Krueger R. R., Trokel S. Quantitation of Corneal Ablation by Ultraviolet Laser Light, Arch Ophth. 1985, pp 1741–1742) that a value intermediate between the threshold and saturation values of intensity provides the highest efficiency for material removal. In the case of the present invention, radiation intensity levels above the saturation value (but below the intensity level where thermal damage occurs) are contemplated in order to reduce the effect of the energy variations that can occur temporally and spatially in the cross sectional laser beam and in order to bring the final ablated surface curvature as close as feasible to that of the caustic.

Figure 2:
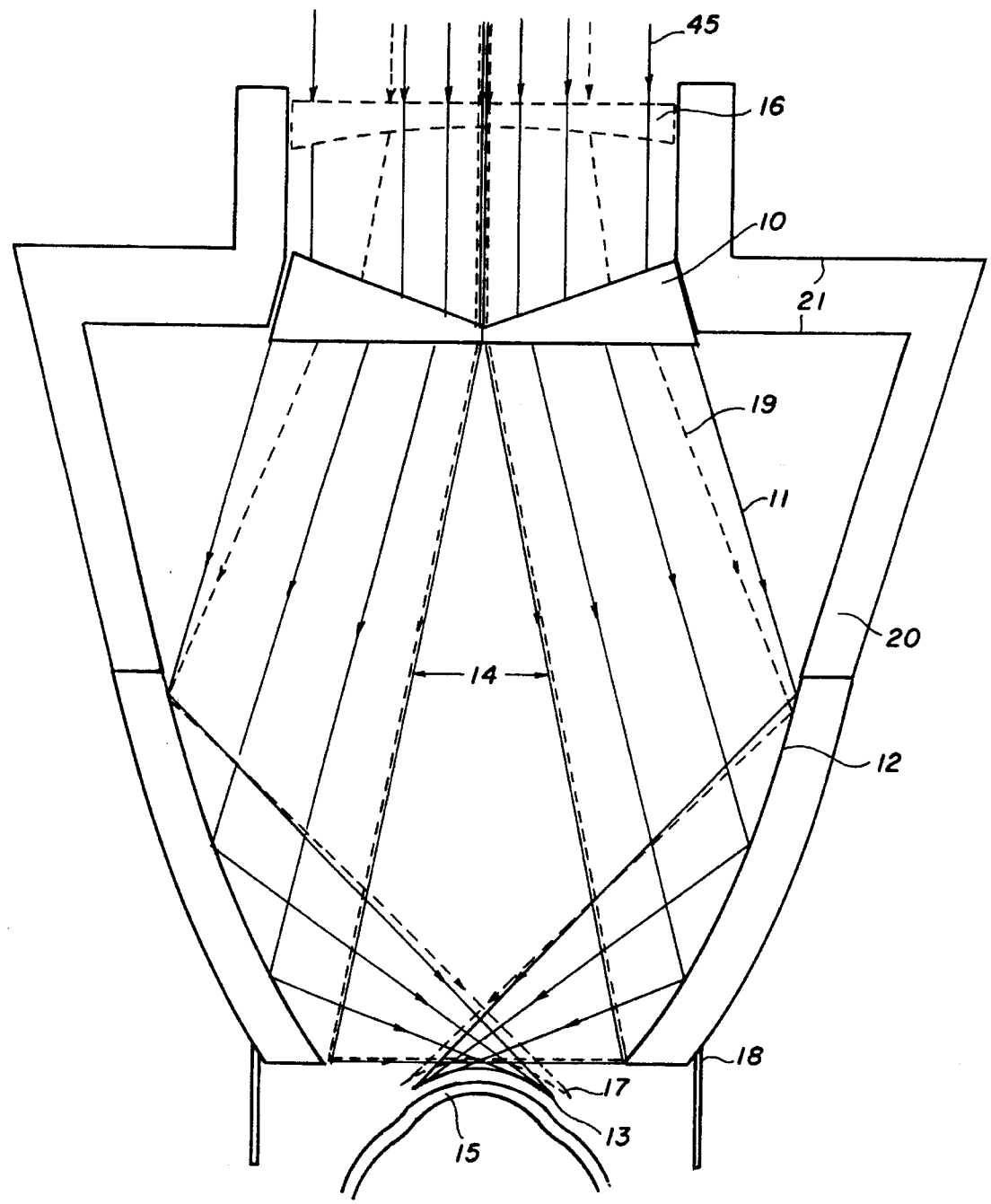
FIG. 2 shows the axicon lens and aspheric mirror assembly and illustrates their function in the preferred embodiment.

The essence of this invention is the catadioptric system comprising the combination of axicon lens and mirror which accomplishes the formation of the caustic surface having near uniform radiation intensity. FIG. 2 shows the preferred embodiment of the axicon-mirror combination: The axicon lens 10 refracts the input beam of radiation 45 into a hollow cone bounded by indicated rays 14 and 11. The volume bounded by rays 14 is a null-energy cone, that is, devoid of radiation and thereby the cornea 15 is protected from any radiation prior to entering the boundary of the caustic 13. The mirror 12, which is a first-surface mirror having a broad band aluminum magnesium fluoride coating, reflects the axicon rays to form the caustic 13.

The housing 20 collinearly aligns the lens 10 and mirror 12. The material constituting housing 20 is preferably transparent to enable visual monitoring of the cornea 15. In particular, a flat optical section 21 permits undistorted viewing of the cornea and/or interferometric monitoring of the cornea. A cylindrical shield 18 which is also transparent to visible light, blocks any excimer laser radiation beyond the caustic field. The diameters of the mirror 12 and the housing 20 are made small enough at the end in proximity with the cornea to permit in vivo corneal ablation unobstructed by facial anatomical features. It is also possible to include a means for conducting optical interferometry of the cornea during the ablating process using commercially available devices (e.g.: WYCO Corp., Micro-maps Corp., Zygo Corp., Chapman Instruments).

Figure 3A:
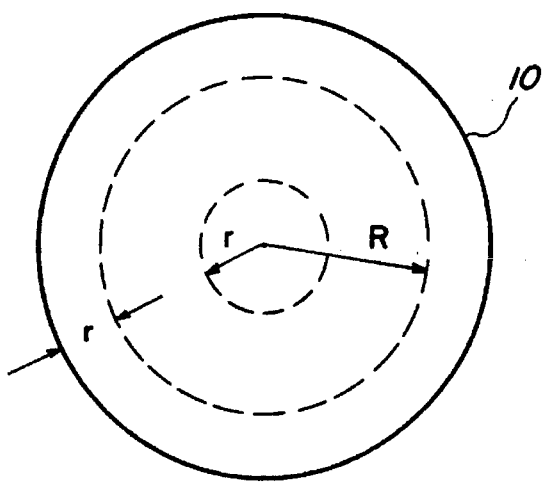
FIGS. 3A, 3B and 3C illustrate the inherent property of the axicon-mirror combination in achieving a uniform intensity caustic surface.
Figure 3B:
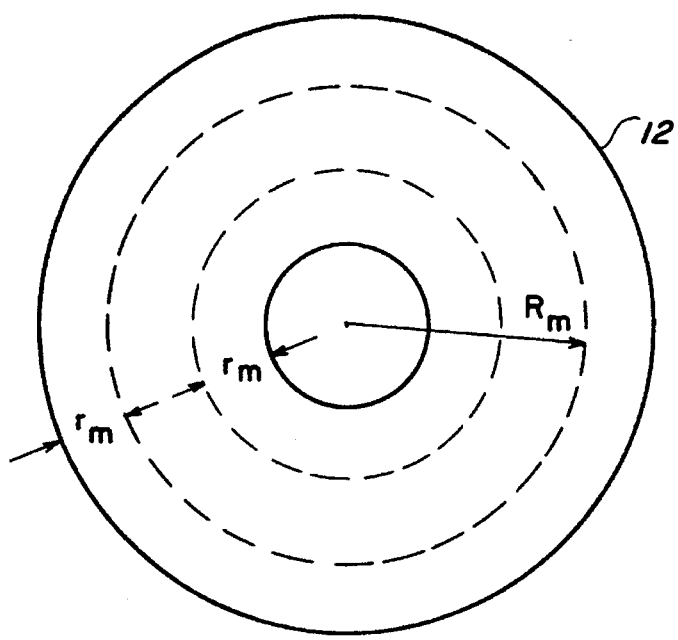
Figure 3C:
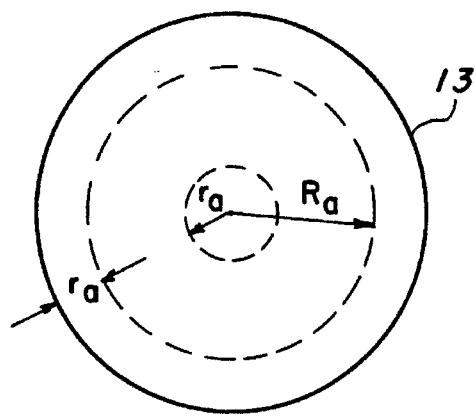

In illustration of the principle of operation whereby the caustic surface 13 achieves uniform radiation intensity, FIG. 3A shows the plan or axial view of the axicon lens 10, FIG. 3B shows the axial view of the mirror 12, and FIG. 3C shows the axial view of the caustic surface 13 Two regions of uniform radiation intensity falling on the axicon are considered. The first is a small circle of radius r centered on the axicon/optical axis; the second is an annulus of width r at a peripheral distance of R. As a result of the unique refractive property of the axicon, all of the radiant energy at the center of the axicon is refracted in the form of an annulus of width $r_m$ around the hole in the mirror as shown. The mirror 12 then reflects the radiation coming from the central circle of radius r of the axicon onto the caustic surface 13 in the shape of a circle of radius $r_a$. In a similar fashion, the peripheral annulus of radiation from the axicon is incident upon the mirror in the form of an annulus of peripheral distance $R_m$ and width $r_m$ which is then reflected by the mirror onto an annulus of width $r_a$ at a peripheral distance of $R_a$ on the caustic. Therefore, the inherent function of axicon and mirror catadioptric system is to translate the uniform beam of laser radiation 8 into a caustic surface of uniform intensity.

Regarding the matter of producing a range of different caustic curvatures, FIG. 2 illustrates, using the ray lines 19, how a different curvature caustic 17 can be produced by the addition of a diverging or negative supplementary lens 16 (all shown in dashed lines).

The use of supplementary lenses having spherical surfaces to vary the radius of curvature of the caustic has several significant limitations. The first of these is the variation of radius of curvature (RC) between the axial and peripheral regions of the caustic. If the RC of the caustic is to be increased, a diverging or negative supplementary lens which further diverges the rays of the axicon is used; conversely if the RC of the caustic is to be reduced, a supplementary lens which is converging or positive and thereby reduces the divergence of the axicon, is used. A spherical positive lens, when designed to produce the desired RC at the center, or on the axis of the caustic, results in a considerably reduced RC at the periphery of the caustic. A spherical negative lens with the desired central RC has a corresponding increase in the RC at the periphery of the caustic. In some cases, such changes in the RC may actually be desired, but the problem is that there is no control of the RC without going to some sort of aspherical surface on the supplementary lenses. Another limitation of the spherical supplementary lens is that of not being able to maintain a fixed radius of the caustic field. For example, a positive supplementary lens would reduce the maximum diameter of the caustic, and this in turn would result in a higher caustic radiation intensity. A further limitation relating to both economy and flexibility in terms of creating a customized caustic, is the large number of supplementary lenses, either spherical and aspherical, that would be needed to provide for the variation occurring in human corneas.

Figure 4A:
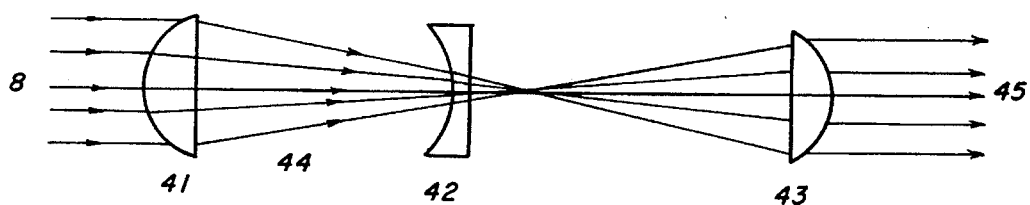
FIG. 4 views the three lens decollimating device associated with the preferred embodiment and shows two arrangements illustrating functionality.
Figure 4B:
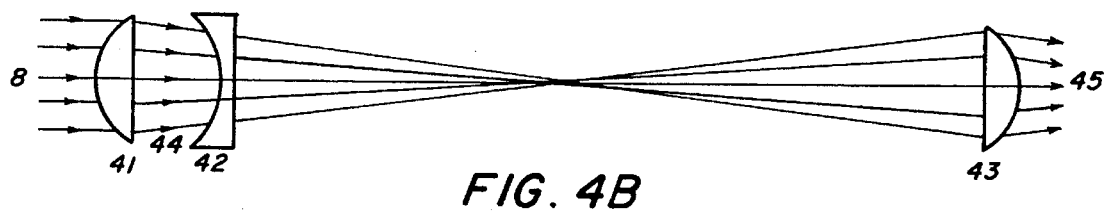

As a solution to this problem, a means was sought to avoid the aforementioned limitations and do so with as few optical elements as possible in order to avoid radiation attenuation. Such a means is shown in FIG. 4 and is called a decollimating device or decollimator. It consists of two plano-convex lenses and one plano-aspheric lens located between the collimated laser output beam 8 and the axicon lens 10. Beginning with an initial spacing between lens 41 and lens 43 so that the of output rays 45 are approximately collimated without the aspheric lens 42, then an axicon-mirror catadioptric system design is selected that produces a caustic field of a desired nominal RC. Next, another radius of curvature of the caustic field is selected, and for the given axicon-mirror combination, the set of ray angles and their intersection on the axicon needed to produce this new caustic field is calculated by means of an iterative algorithm. Then, for this ray set, the aspheric lens 42 is spaced closely to the first lens 41, and the third lens 43 is spaced to provide about the desired output beam diameter, as shown in FIG. 4b. The reason for the close spacing of lens 41 and lens 42 is that when they are separated, only the more central portion of the aspheric lens will capture the laser rays converged by lens 41 as illustrated in FIG. 4a, thus the aspheric surface will result in less refraction of the rays 44, so that the rays 45 entering the axicon will be nearly identical to the collimated laser rays 8 thereby producing a caustic surface having nominal RC. Then, in general, motion of the aspheric lens 42 between lens 41 and lens 43 will result in a continuous variation of caustic radius. Spacings where the radiation beam is converged to a degree where the intensity of the radiation results in material damage to the lenses, must be avoided. To achieve the stated objectives, all three lenses will need to be moved to achieve a given caustic RC and a caustic radiation field of fixed diameter.

A computer evaluation of the three lens system shows that aspherical caustic surfaces ranging from oblate ellipsoids to hyperboloids may be generated. Determination of the needed spacings to produce the desired caustic surface may be calculated by computer.

The range of caustic curvatures produced by the decollimator can be extended by the insertion of supplementary lenses. For example, if a given decollimator spans a diopter range from 38 to 48, a diverging supplementary lens could expand the lower limit of 38 down to, say, 34; a converging supplementary lens could expand the higher limit of 48 to, say, 52.

Another use for supplementary lenses has application for astigmatic patients whose source of astigmatism is not (only) the cornea of eye, but also the lens of the eye. In this case, the invention can correct for this lenticular astigmatism by means of supplementary lenses in the form of cylindrical lenses (or lens) placed between the decollimator and axicon-mirror combination. This will result in a cylindrical surface being superimposed upon the cornea to cancel out the cylindrical component of the lens of the eye that is producing the astigmatic refractive error.

Variations within the context of the preferred embodiment include making the mirror 12 spherical and incorporating the missing asphericity on the axicon and/or on one or more of the lenses within the decollimator. Because the mirror 12 has an optical accuracy requirement some two to four times higher than the lenses of the optical system, allowing the mirror to have a spherical surface, which is much easier to fabricate, is of considerable significance in regard to cost reduction.

Figure 5:
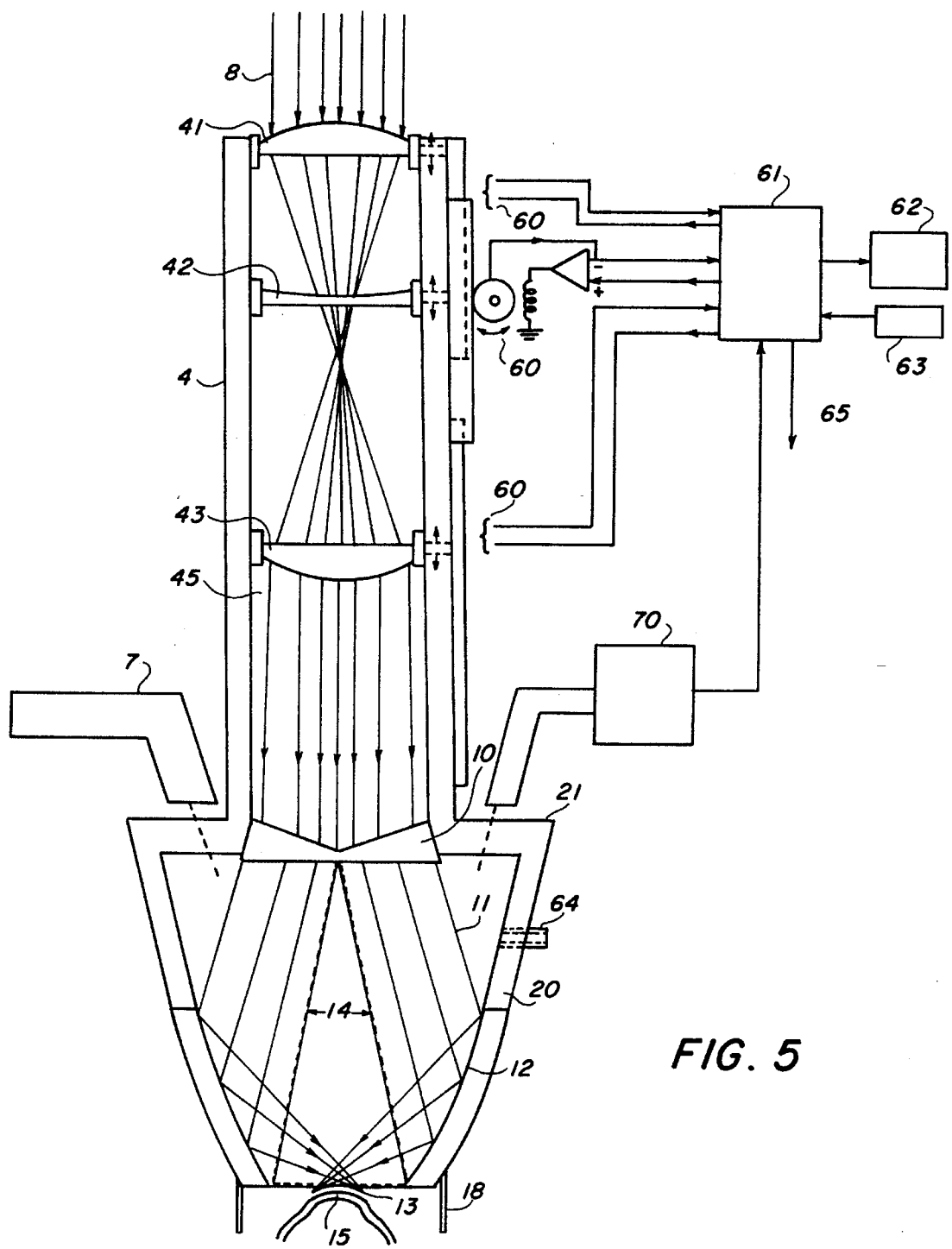
FIG. 5 shows the total optical system of the preferred embodiment with a summary of computer monitoring and control.

FIG. 5 shows the total optical system of the preferred embodiment as an integral unit. Ancillary to the optical assemblage 4 of decollimator and axicon and mirror catadioptric system, are devices for monitoring and control. The close focusing telescope or microscope 7 and the interferometer 70 have visible access to the cornea 15 through the optical flat region 21 of the housing 20. An example of a means for changing the spacing of lenses in the decollimator is the set of three electric servomotor rack and pinion drives 60 each of which controls the axial position of a decollimator lens through either a slot in the housing 20 or two permanent magnets, one magnet which holds the lens and the other external to the housing 20 and connected to the drive 60; the drives 60 are staggered around the housing 20 to avoid interfering with one another. A computer 61 receives the position feedback signals produced by the servomotors of the drives 60 and then issues the signals to reposition the decollimator lenses. The computer, by either executing the ray-tracing calculations or by means of a table look-up and interpolation program, solves for the caustic surface 13 which can be viewed on the display 62 and compared with the preoperative corneal surface. Required changes in the shape of the caustic are inputted into the computer through the command interface 63. An additional function of the computer 61 can be the real time control of the laser pulsing 65 in response to the real time interferometer measurements of the cornea to insure that the laser will fire only when the instantaneous position of the cornea is within permitted tolerances. Removal of ablation products is facilitated by pressurizing the axicon-mirror cavity through a vent tube 64 so that air, or some appropriate inert gas, is forced out through the space between the bottom of the mirror 12 and the cornea and then out past the shield 18.

Figure 6:
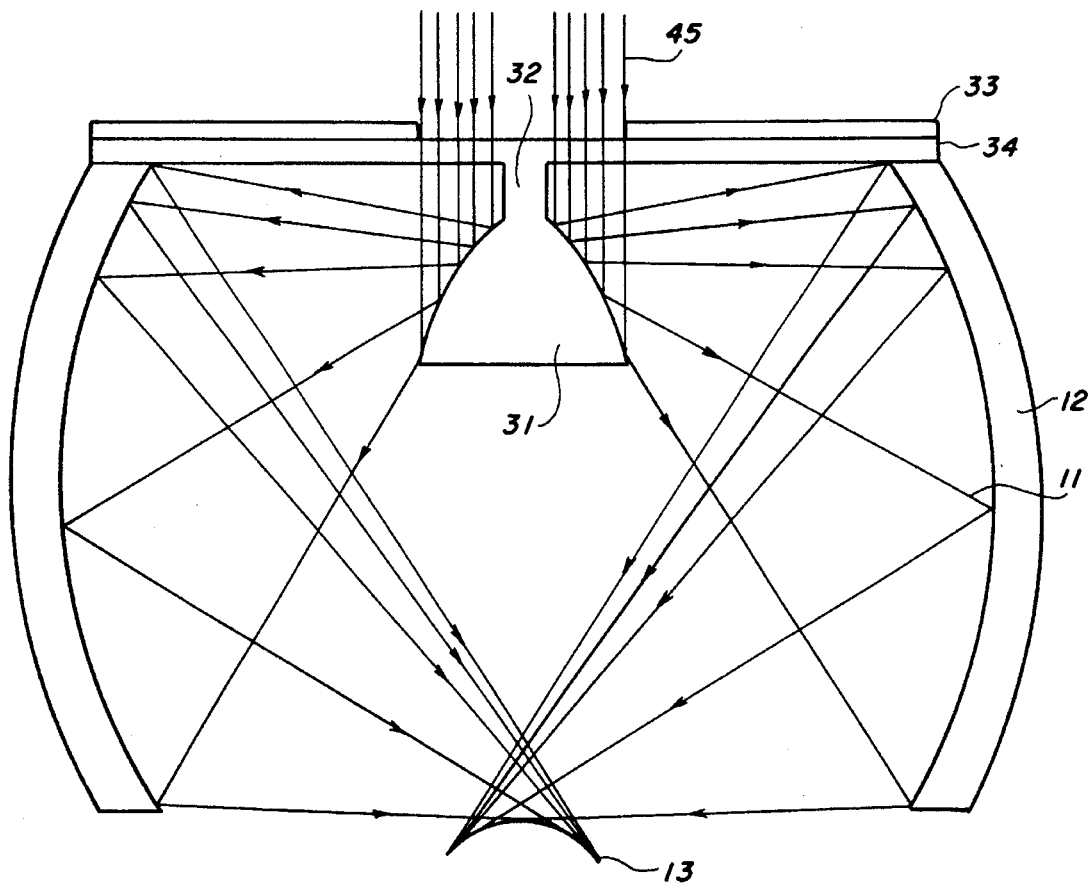
FIG. 6 shows a two mirror alternate embodiment.

The essential method of the invention, which is the creation of a desired caustic surface, can be achieved by other embodiments. One of these involves the replacement of the axicon lens 10 by a mirror 31 as in FIG. 6, which, in combination with the mirror 12, produces the desired uniform radiation intensity caustic surface 13. This property is effectuated by a variation of curvature so that near the smaller cross sectional diameter (apex) of the mirror 31, a greater area of the laser beam is intercepted than is intercepted at the larger cross sectional bottom diameter. Mirror 31 is rigidly aligned with mirror 12 by means of a design similar to an inverted wine goblet, with stem 32 connecting to a transparent optical disk 34 (the base) having low radiation attenuation. An aperture 33 constrains the beam of radiation 45 to the mirror 31 surface only. This embodiment requires a higher precision of alignment than the preferred embodiment of FIG. 2, but has the advantage that the shape of the caustic surface 13 is independent of the wavelength of radiation used.

In the further embodiment shown in FIG. 7, the mirror 12 is replaced by a solid lens 71 consisting of three distinct optical regions. This lens is designed so that axicon rays entering the front surface 72 are refracted to the side-wall 73 at a sufficiently oblique angle to insure total internal reflection. The rays so reflected are directed to the rear optical surface 74 having an aspheric surface so shaped as to refract the reflected rays to form the desired caustic surface 13. As shown in FIG. 7, the axicon rays are substantially parallel and impinge on the side-wall 73 at a constant angle; the side-wall 73, although shown straight-sided, is also permitted to be curved. This embodiment avoids the necessity of having to deposit a reflective coating, but introduces two additional optical surfaces.

FIG. 8 shows a method of reducing the total number of optical surfaces from five to three through the use of a single thick lens 75 of high transmissibility (e.g. magnesium fluoride) having thereon imposed the axicon, side-wall total internal reflection mirror, and rear lens optical surfaces. In the interests of economy and minimizing radiation attenuation through the lens, the distance between the front (axicon) surface 76 and the rear surface 74 should be maintained to less than about one inch. This embodiment has the additional advantage of providing a catadioptric system which is pre-aligned.

Figure 9:
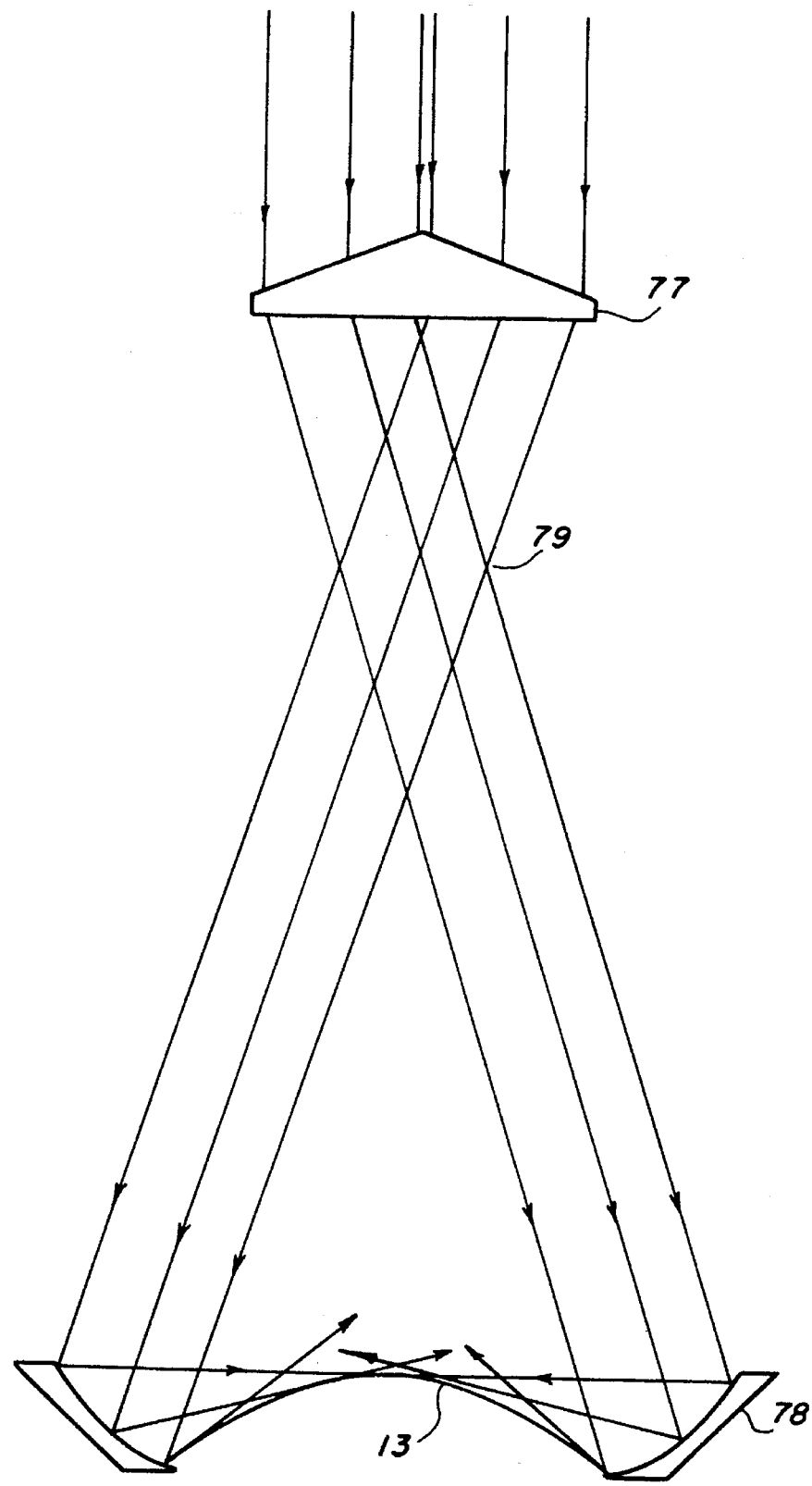
FIG. 9 shows an alternate embodiment using a convex axicon.

Another alternate embodiment of the axicon-mirror catadioptric system appears in FIG. 9. Here, the axicon lens 77, rather than being a negative/diverging lens as it appears in the foregoing embodiments, is a positive/converging type. The mirror 78, corresponding to mirror 12 of the preferred embodiment, has a hole of sufficient size through which the cornea protrudes. Here, in contrast to the preferred embodiment, the caustic surface is formed between the axicon lens 77 and mirror 78. The mirror 78 is restricted to a smaller size than in the foregoing embodiment in order to fit over the sclera and below the apex of the cornea. The criss-crossing axicon rays 79 permit the caustic surface 13 to be produced with uniform intensity because of the following sequence: Rays from the center of the axicon fall on the top edge of the mirror which in turn reflects the rays to the axis of the caustic surface (and cornea); rays from the periphery of the axicon fall on the bottom of the mirror which in turn reflects the rays to the periphery of the caustic field (and cornea). An advantage to this embodiment is that a convex axicon is easier to fabricate than a concave axicon; the main disadvantage is the lack of flexibility in fitting different diameter corneas with a single mirror and the restriction in the range of curvatures that can be accommodated using the decollimator.

Within the intent of the invention, it is possible to replace the axicon lens and mirror with a fresnel-type lens and a fresnel-type mirror provided the grating spacing is sufficiently fine.

Also within the intent of the invention, the decollimator may be comprised of more than three lenses and/or more than one aspherical surface. As an example of a reason for such an increase might be the desire to maintain the separation between lens 41 and lens 43 constant; to do so a fourth lens with an aspheric surface in conjunction with aspheric lens 42 could be designed for this purpose. In general, the flexibility of design increases with the number of lenses subject to the limitation of radiation losses or attenuation through the decollimator.

Figure 10:
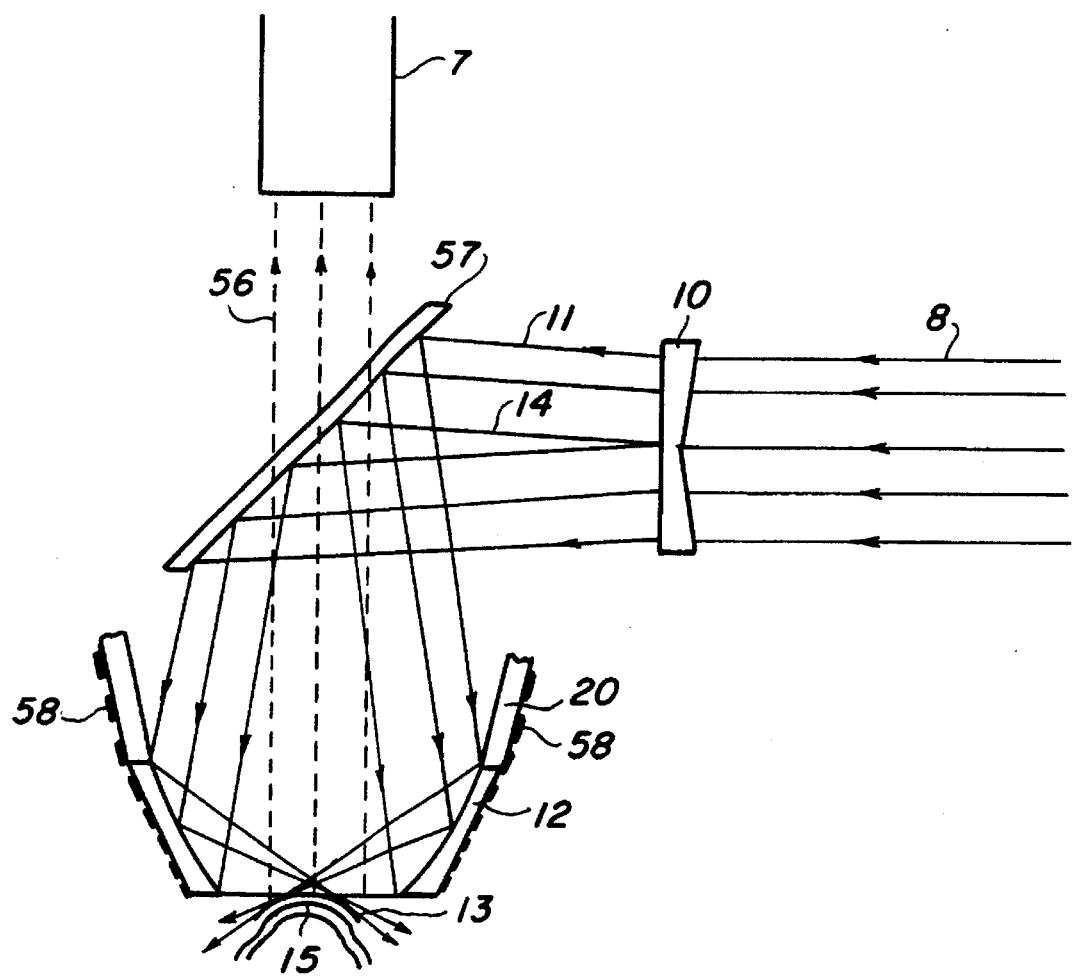
FIG. 10 shows a laser radiation redirection means consisting of a planar mirror between axicon lens and aspheric mirror.

A modification applicable to most of the foregoing embodiment is given in FIG. 10. A planar mirror 57 with a dielectric coating having nearly total reflectance to the laser radiation while being essentially transparent to visible light, is inserted at a 45 degree angle between the axicon lens 10 and the mirror 12. The required perpendicular displacement of the mirror 12 with respect to the axicon lens 10 permits a direct view of the corneal surface along the optical axis of the cornea. This availability of a direct axial view of the corneal surface facilitates the use of the aforementioned microscope 7 or interferometer 70 means as shown by the passage of visible light rays 56 through the mirror 57. In addition, if the body of the mirror 12 is visually transparent to visible light like the planar mirror 57, and further if the aluminum magnesium fluoride mirror surface of the preferred embodiment is replaced with a dielectric coating similar to the planar mirror 57, then a series of visually opaque bands 58 may be placed coaxially around the outside of the mirror 12 and extended along a visually transparent housing 20. Outside light causes a reflection of these bands from the corneal surface 15 which are viewed through a calibrated reticle within the microscope means 7, thereby providing a means for conducting keratometry during the ablation process.

Because the surgical application of the invention results in the removal of varying amounts of corneal tissue depending on the degree and nature of the refractive correction required, a thorough pre-operative examination of the cornea is necessary including the determination of corneal thickness (pachymetry), curvature of the cornea (keratometry, photokeratoscopy), and cornea tissue examination (histology). With the information obtained from these tests, the desired postoperative curvature and the maximum allowable depth of corneal ablation is established, along with the determination of whether or not to remove the epithelial layer from the cornea prior to laser ablation.

To this point in the description of the invention, the principles and various apparatus embodiments for generating desired caustic surfaces of uniform radiation intensity have been presented. Overall apparatus embodiments for conducting photo-ablative refractive keratectomy are covered in prior art (e.g. L'Esperance, Marshall, et.al.). The present invention necessarily incorporates the same elements, i.e. a laser source of radiation, an optical means for modifying the laser radiation, and a means for constraining the in vivo cornea or in vitro target ablatable material. In vivo corneal ablation imposes stringent demands on the constraining apparatus in order to avoid an off-centered ablated corneal surface. By means of requiring the patient to maintain steady fixation of a point, and/or applying a vacuum ring to avoid eye motion, acceptable refractive correction has been achieved using the en face method. For the present invention, in addition to maintaining the fixed radial positioning necessitated by the en face method, the axial position of the cornea must also be fixed.

Figure 11:
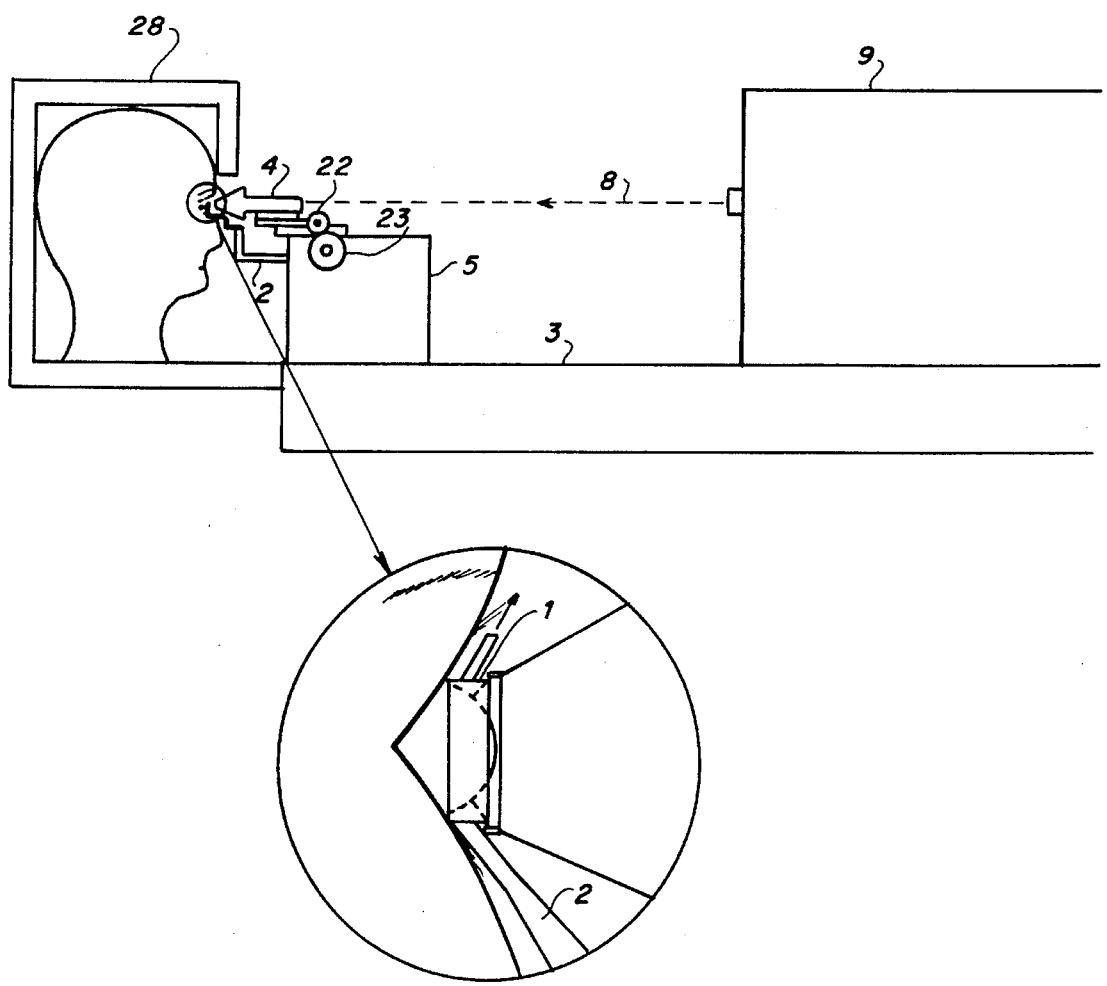
FIG. 11 illustrates the basic components comprising the overall apparatus for effecting in vivo corneal ablation.

An example of an overall apparatus for providing the necessary corneal fixation and caustic surface axial advancement is shown in FIG. 11. In this implementation, the laser 9, and the pedestal 5 are both firmly fixed to a solid frame of reference or bench 3. The total optical assembly 4 consisting of concatenated decollimator and axicon-mirror combination catadioptric system, is attached to a precision rack and pinion mechanism 22 mounted atop pedestal 5. Mounted on the front of pedestal 5 is a bracket 2 which is attached to a vacuum ring 1. The patient's head is positioned so that the vacuum ring 1 fits on the sclera of the eye. Then a hood 28 containing a conformable foam material is moved into position to constrain the patient's head and the bottom of the hood anchored to bench 3. The vacuum to the vacuum ring 1 is activated and small adjustments are made to the patient's head to eliminate any distortion-causing stresses to the cornea. The rack and pinion mechanism 22 can be either manually advanced or automatically advanced by means of an electric motor 23 to bring the caustic surface formed at the end of the optical assembly 4 into proximity with the cornea.

Once the desired postoperative corneal profile is established, the spacings of the lenses within the decollimator are adjusted to yield the desired caustic surface 13.

Using the apparatus of FIG. 11, after the aforementioned fixation of the cornea, the laser 9 is activated and the rack and pinion 22 is used to advance the caustic surface 13 into just making contact with the cornea 15; initial corneal contact with the caustic surface radiation is evidenced by the presence of a light-blue visible fluorescence. The motor 23 is then engaged to drive the rack and pinion 22 and hence the optical assembly 4 at a predetermined advance rate into the cornea. The ablation process is monitored by the aforementioned visual microscope and/or interferometer means.

Within the intent of the invention, a number of variations are possible for bringing the caustic surface 13 into contact with the cornea to the degree of accuracy enabled by the apparatus of FIG. 11. For example, the mechanical rack and pinion 22 and associated electric motor 23 may be replaced with a precise linear stepping motor or electromagnetic solenoid, or a hydraulic or pneumatic piston. Also, the piezoelectric and magnetostrictive phenomena whereby mechanical motion is achieved by the application of electric and magnetic fields, respectively, may be employed to achieve the incremental advance of the caustic surface 13.

A perturbation that is inherent in any tangential in vivo ablation method involves the unavoidable tremor of the human body related to the beating of the heart and the autonomic nervous system. Such involuntary spasmodic activity can manifest itself as variations in the position of the cornea in the axial direction, even as the conscious patient is maintaining good visual fixation. Whether or not such variations are of high enough amplitude to result in a degradation of the ablated surface is probably patient dependent. The stability afforded by the vacuum ring 1, in conjunction with the remainder of the apparatus of FIG. 11, should obviate any undesired corneal motion effects.

Figure 12A:
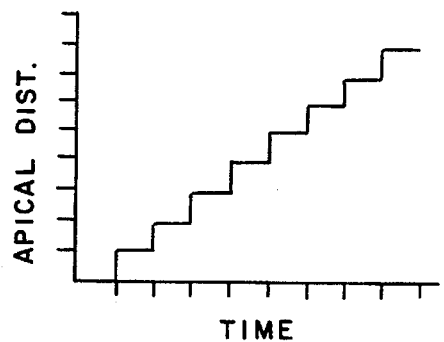
FIG. 12 illustrates corneal spatial perturbations and shows a means for obviating their effect.
Figure 12B:
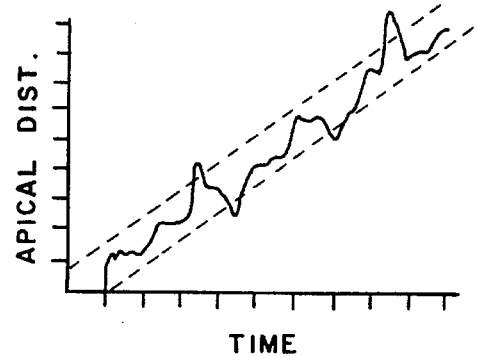
Figure 12C:
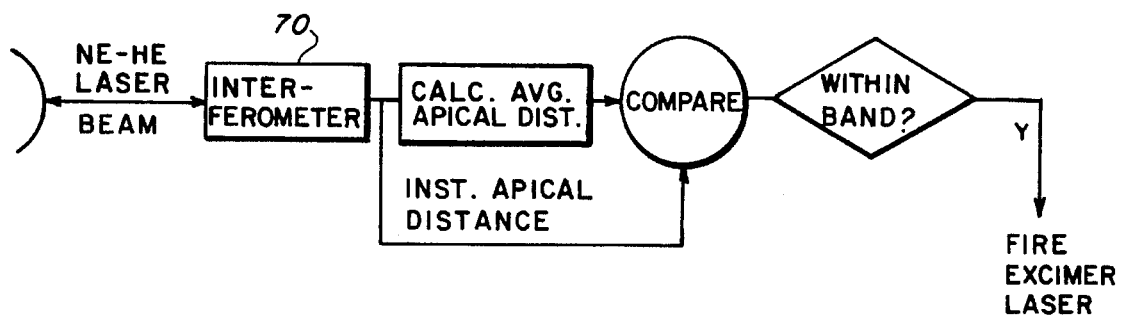

An alternate means for obviating the effect of corneal tremor is diagrammed in FIG. 12. A helium-neon laser based direct phase-detecting interferometer 70 measures the apical distance of the cornea as the ablation process is proceeding. Because only a small area near the apex of the cornea is being measured, the interferometer 70 can make distance measurements at a frequency at least three times greater than the excimer laser pulse rate, and, if the cornea is perfectly still, the apical distance for myopic correction increases as a linear staircase, each step occurring with each excimer laser pulse as shown in FIG. 12*a*. However, with the presence of tremor, a rising but ragged distance with respect to time curve results as in FIG. 12*b*. The following is a remedy to this problem of the laser firing when the surface of the cornea is not in the intended position: First, these instantaneous interferometer measurements of apical distance are averaged and an allowable band about this average is specified as shown by the dashed lines in FIG. 12*b*. Then, if an instantaneous apical distance is outside of the allowable band, the firing signal to the excimer laser will be delayed until the apical distance is within the band. The procedural block diagram for doing this appears in FIG. 12*c*.

An example illustrating the application of the invention to corneal modification follows: Assume a myopic eye needing a correction of some 2 diopters. This translates to a depth of ablation along the axis of the cornea of some 25 um for a spherically reshaped zone of about 6 mm diameter. Studies have found that corneal tissue is ablated at about 2 microgram (ug) per pulse for a 193 nm energy intensity of about 500 mJ/cm$^2$. Assuming this energy intensity per pulse at the boundary of the energy field, then each pulse removes some 0.2 um of tissue, which requires 125 pulses for total time of 12.5 seconds at 10 pulses per second.

An essential part of this invention is the calculation of the optical surfaces. In addition to the axicon, at least one of these surfaces must be aspheric and because of this and because the formation of the caustic surface is outside of the province of image forming (telescopes, microscopes, cameras, etc.) optical technology, specialized computational algorithms had to be created. By defining the constraints and the variables of the algorithms, the assertions of performance made here-to-fore for the invention may be ascertained.

Figure 13:
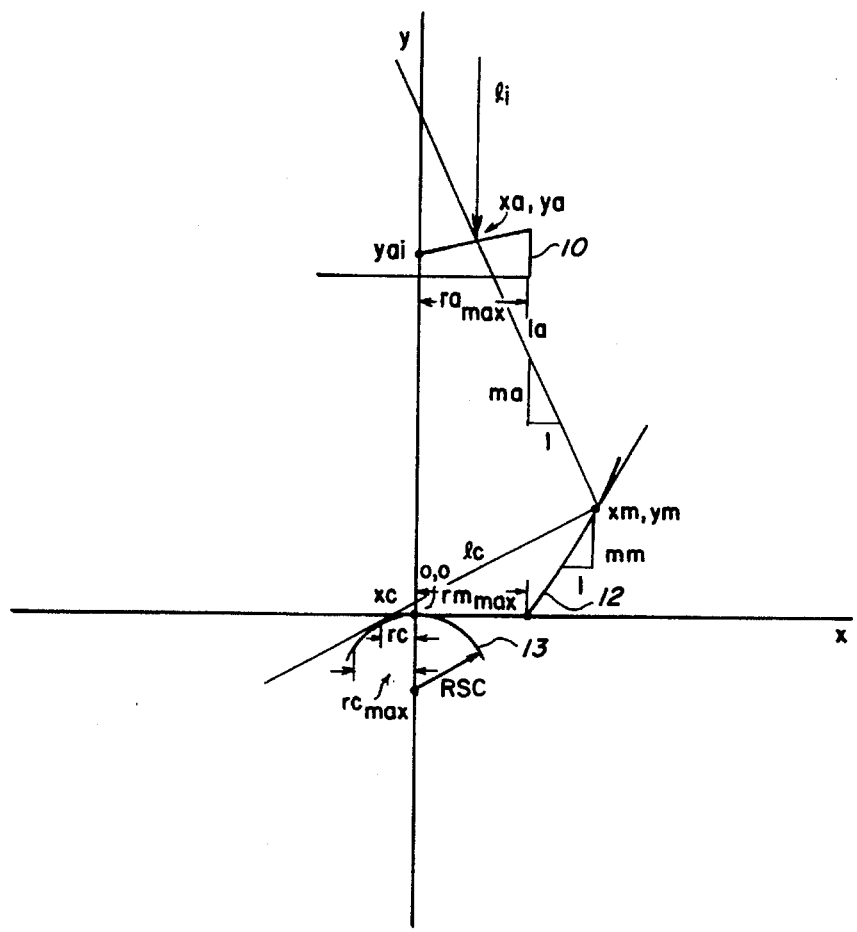
FIG. 13 shows the geometrical considerations involved in axicon and mirror design.
Figure 14:
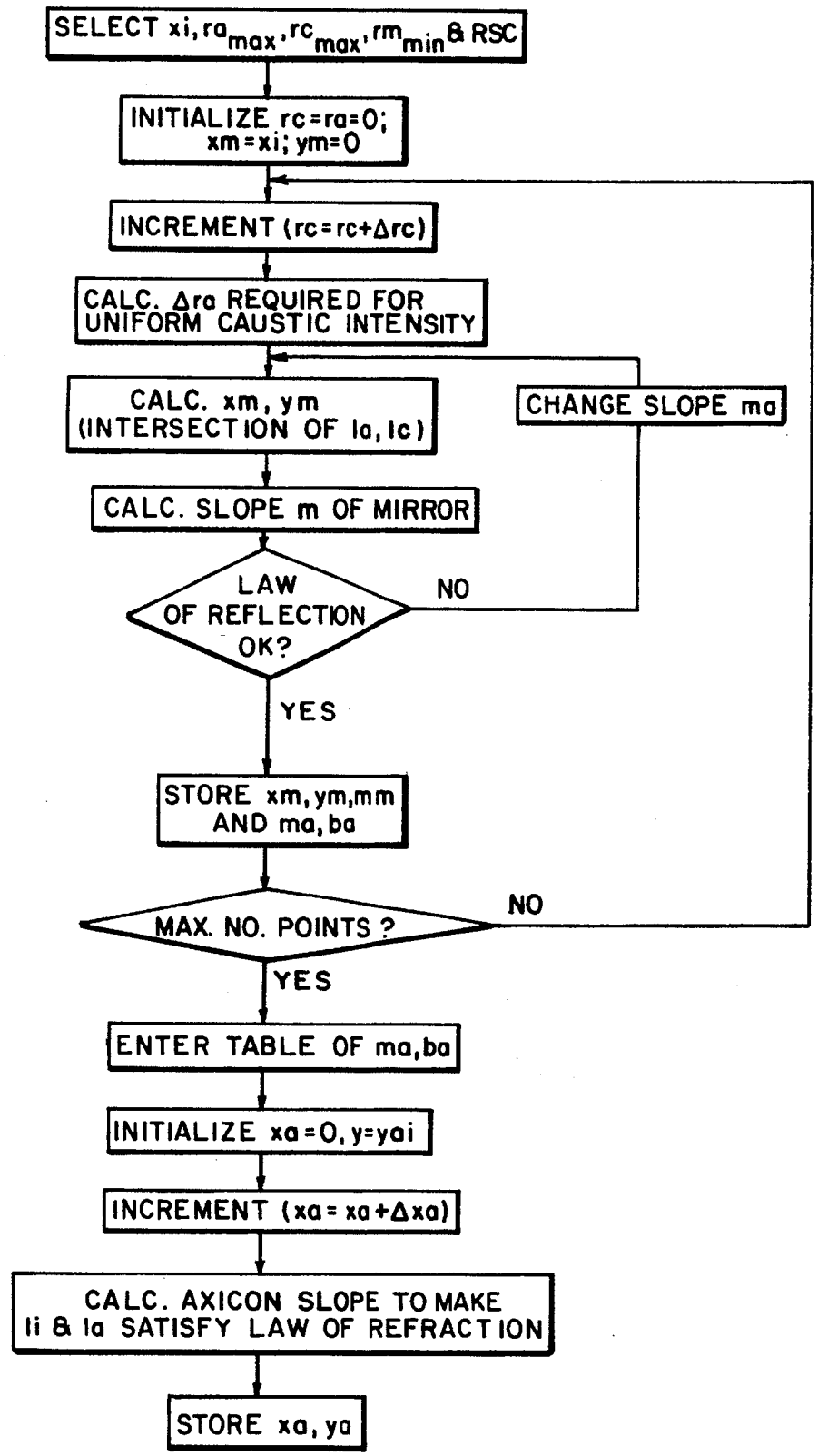
FIG. 14 is a flow chart of the algorithm for solving for the meridional coordinates of axicon and mirror.

Beginning with the axicon lens 10 and (aspheric) mirror 12, the constraint is to produce a caustic surface 13 having uniform radiation intensity. In FIG. 13, the cross section of axicon, mirror and caustic are shown. For the first letter of the symbols in FIG. 13: r is a radial distance from the optical axis, l is a line specifying a ray, m is the slope of a line, b is the intercept of a line on the y axis, and x and y are distances from the specified origin point O,O of the cartesian coordinate system; for the second letter in the symbols: a refers to an axicon ray, m refers to the mirror, c refers to the caustic surface. A nominal caustic surface 13 curvature is first specified and it may be either spherical or have an aspherical curvature appropriate for alleviating the presbyopic condition. Next, a tangent line to the surface near the apex or axis is drawn and from this starting point, the initial x coordinate at the bottom of the mirror is selected, consistent with the initial wedge angle of the axicon so that the central axicon ray intersects with this initial mirror coordinate point. The diameter of the axicon is next selected, and it will normally be about the size of the small dimension of the laser beam cross section. Corresponding to the maximum radius of the axicon, the maximum radius of the caustic is selected, and for corneal refractive correction, this will normally be some 30 to 50% smaller than the maximum radius of the axicon. Given the ratio between maximum axicon and maximum caustic radius as rac, the requirement of uniform radiation intensity is met by forcing the condition that the radiation energy contained within a circular cross section of radius xa on the axicon is transferred to a circular cross section of radius xc on the caustic surface such that the ratio of radiation intensity on the caustic to the radiation intensity leaving the axicon is equal to rac$^2$F where F is a factor that accounts for the surface curvature of the caustic. With these constraints, a line la (ray) is drawn through the point xa on the axicon and the slope of la is iteratively changed so that it intersects with the caustic tangent line to define a point on the mirror where the law of reflection is obeyed. The process is continued at a small enough increment to be assure that the surface can be defined to within an accuracy about equal to the wavelength of the laser radiation. This procedure generates the meridional profile of the mirror surface along with the required set of rays from the axicon. Then by calculating the incremental surface slopes of the axicon necessary to refract the collimated laser beam to produce each ray of the required set, the meridional profile of the axicon is thereby solved. FIG. 14 gives the flow chart describing the algorithm for determining the coordinates of both the refractive surface of the axicon and the reflective surface of the mirror.

The technology that is used to fabricate the aspherical optical surfaces is commonly referred to as a diamond turning process. These computer controlled machines use as their input, not the coordinates generated by the algorithm of FIG. 14, but the coefficients of a high order polynomial that is an accurate curve fit to the coordinate points generated. Therefore, the final stage in the design process is to curve fit these points by means of a least-square technique. The form of the polynomial is $y=a_1x^2+a2x^4$ . . . For the prototype design used in the proof of principle of this invention, 1; coefficients were used for the design by OFC Corporation, Diamond Turning Div. to fabricate the mirror.

The foregoing algorithm for the concurrent design of axicon lens and mirror assures a caustic surface radiation intensity uniformity within a tenth of a percent at the nominal or design caustic surface curvature. In theory, perfect uniformity of intensity could be achieved for the caustic surface because of the additional degree of freedom provided by the axicon lens of this invention which permits simultaneously attaining both the desired caustic curvature and uniformity of caustic surface radiation intensity.

The axicon-mirror combination and decollimator in combination constitute a ninth degree of freedom system having, as it does in the preferred embodiment of the invention, a total of four lenses and one mirror. Therefore, if it is desired to replace an aspherical surface with a spherical surface, the needed asphericity can be transferred to some other spherical surface. For example, to achieve the objects of the invention through the use of a spherical mirror rather than an aspherical mirror 12, the required effective asphericity may be added to the decollimator lens nearest the mirror. This can be accomplished by modifying the algorithm of FIG. 14 so that the ray line 1a as well as 1c is an independent variable (because the spherical surface of the mirror is fixed). Then, the ray line 1i, which in this case is the ray between the axicon and the nearest decollimator lens to the mirror, is varied in slope and position in the same manner as the line 1a in FIGS. 13 and 14.

Figure 15:
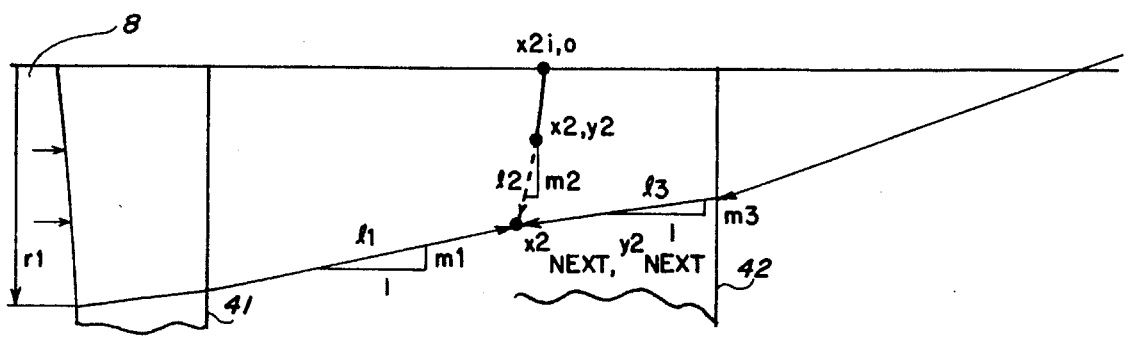
FIG. 15 shows the geometrical considerations for the design of the decollimator aspherical lens.
Figure 16:
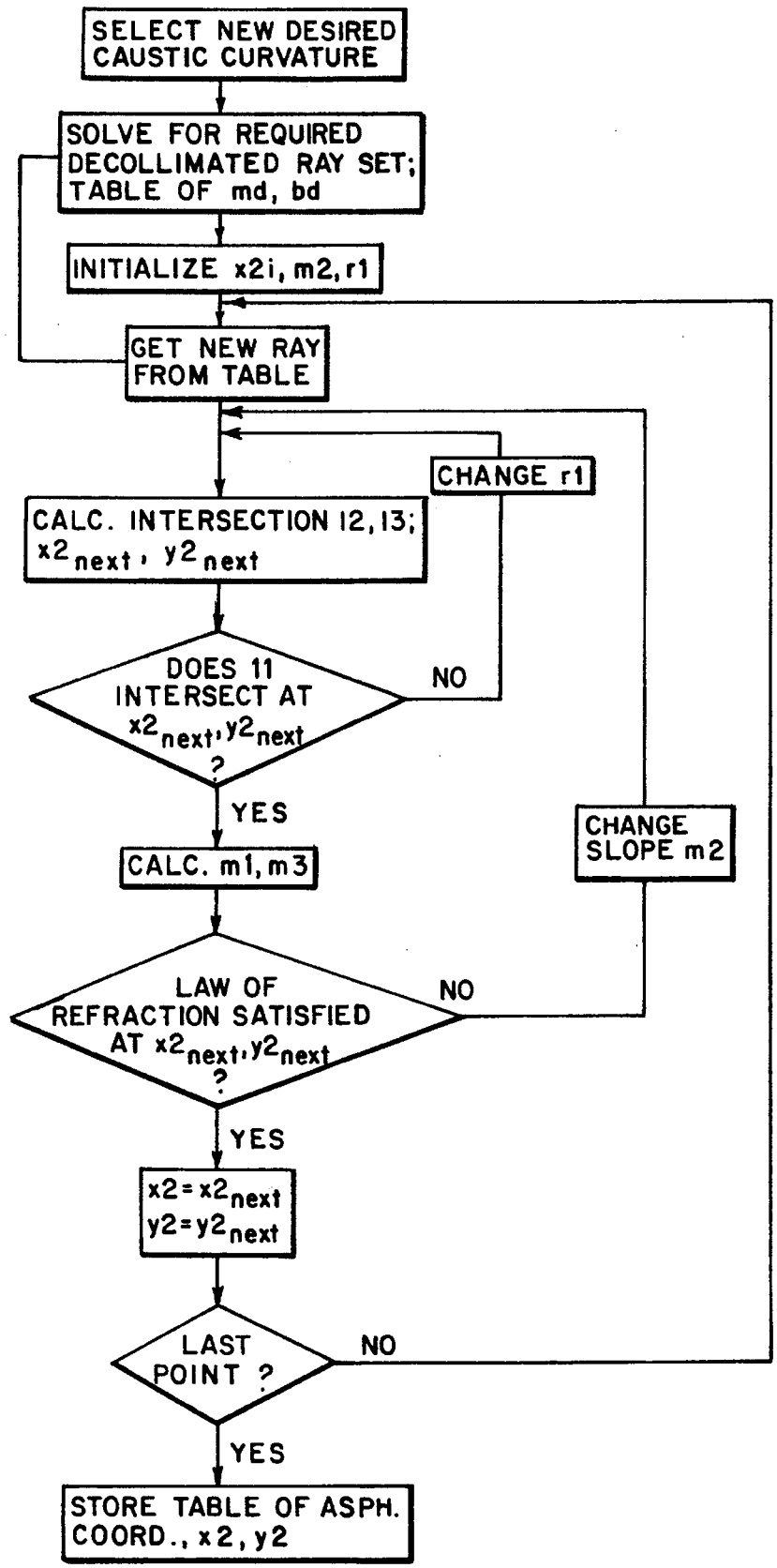
FIG. 16 is the flow chart for solving the meridional coordinates of the decollimator aspherical lens.

The method for the design of the remaining portion of the optical system in the preferred embodiment, the decollimator, is similar to the algorithm of FIG. 14. In peroration of FIG. 3, spherical lenses 41 and 43 have a curvature and spacing such that the collimated laser beam entering lens 41 emerges from lens 43 with about the same diameter and minimal decollimation due to spherical aberration. Consequently, the collimated beam entering the axicon of the axicon-mirror combination results in the nominal design caustic surface 13 curvature. Then, a new caustic surface curvature is selected having a diopter value differing from the nominal design curvature by about one half the total diopter span planned for the decollimator. In order for the catadioptric system to form this new caustic curvature, the rays entering the axicon must be decollimated by a prescribed amount. This set of decollimated rays is calculated by, in effect, back reflecting the new caustic tangential rays from the mirror to the axicon, whereupon, the rays are refracted through the axicon to form the decollimated set. Next, each ray of this decollimated set is traced back through lens 43 towards lens 41, but before entering lens 41, the ray is intercepted by lens 42 whose surface is yet to be determined. The iterative procedure depicted in FIG. 15 forces one surface of lens 42 to refract the ray towards lens 41 at such an angle that each ray emerges from the left surface of lens 41 collinear with the optical axis, i.e. collimated to match the laser beam. The first letter of the symbols appearing in FIG. 15 follows the conventions of FIG. 13; the second letter (number) refers to the related lens number: 1 is for rays coming from lens 41, 2 denotes the aspheric surface, 3 is for rays coming from/to lens 43, d denotes the required decollimated rays. FIG. 16 is a flow chart for computing the decollimator aspheric lens design.

When the decollimator of the preferred embodiment is used to produce a variation of caustic curvatures over a ten diopter range, the caustic surface radiation intensity varies by about ±35 percent for the particular optical design employed. Such a variation still meets the stated requirement of near-uniform intensity because the nominal radiation intensity is maintained above the saturation value of ablation by about a factor of two so that radiation intensity variations less than two to one are effectively negligible. Within the intent of this invention, any radiation intensity variation across a range of caustic surface curvatures can be made negligible by increasing the number of aspherical optical surfaces.

I claim:

1. A method having a surface area, a desired curvature, and of substantially creating a caustic surface of uniform intensity radiation using a catadioptric device comprising at least one axicon lens, each having a surface and a surface area, and a mirror, said method comprising the steps of:

selecting: (1) a starting coordinate point corresponding to a minimum radial distance from a optical axis for the mirror of said catadioptric system; (2) a ratio of the surface area of the axicon lens, of said catadioptric system, to the surface area of said caustic; (3) the desired curvature of said caustic;

calculating positions of rays through said axicon corresponding to tangential rays which form said caustic that maintain said ratio of areas constant;

varying slopes of said axicon rays so that intersection with said corresponding caustic tangential rays produces the locus of coordinate points of a meridional cross section of said mirror subject to a law of reflection;

calculating said coordinate points for at least one surface of at lease one of said axicon lens to produce a desired set of axicon rays subject to the law of refraction.

2. A method according to claim 1 further including the steps for designing a decollimating means for providing for a continuous range of caustic surface curvatures, said steps including:

selecting a new caustic curvature differing in diopter power from a nominal caustic curvature by about one half a range of caustic curvatures desired to be spanned;

solving for necessary set of decollimated rays required by said catadioptric system to produce said new caustic curvature;

specifying a system of two converging lenses, each converging lens having a curvature and relative spacing to negligibly decollimate a collimated beam;

placing an aspherical lens having a surface between said converging lenses in preparation for calculating the surface of said aspherical lens;

refracting said necessary set of decollimated rays, through said converging lens in proximity with said axicon, to be incident upon said aspheric lens and iteratively calculating a desired of said aspheric lens so that the desired surface of said aspheric lens gives rise to a modified ray set, said modified ray set when directed through the remaining converging lens is refracted to form a collimated beam corresponding to the collimated beam produced by the laser source of radiation.

3. A method according to claim 2 where the step of placing an lens further includes placing additional aspherical lenses for the purpose of achieving additional degrees of freedom in design.

4. A method of photoablative keratectomy comprising the steps of:

selecting a desired corneal surface and adjusting an optical device thereby for producing a caustic surface of substantially uniform intensity radiation capable of ablating to said desired corneal surface;

aligning a photoablative laser coaxially with said optical device and said corneal surface;

controlling extraneous movement of said corneal surface;

activating said laser and onto said corneal surface until said corneal surface is ablated to a desired curvature.

5. An apparatus for ablating a surface of a corneal surface to produce a predefined optical surface thereon, said apparatus comprising:

a source producing a collimated beam of ablative radiation means for directing said collimated beam coupled to said source;

an optical device coupled to said means for directing said collimated beam, said optical device consisting of a decollimator containing lenses, said decollimator including means for creating a decollimated beam, said decollimator coupled to a means for directing said decollimated beam into a system, said system comprising means for forming a continuous, simultaneous three-dimensional caustic surface of substantially uniform intensity, said system also including means for continuously adjusting said caustic surface over a range of curvatures;

an axial advancing means coupled to said system for bringing said caustic surface into proximity with said corneal surface to progressively ablate the corneal surface to a desired curvature;

a support and control means coupled to the optical device for maintaining said material in alignment with said optical device.

6. An apparatus according to claim 5 wherein said catadioptric system is comprised of a spherical mirror and a concave axicon lens, incorporating the asphericity that would normally be required on said spherical mirror to produce the near uniform intensity onto one or more of said axicon lens and at least one of the lenses within said decollimator.

7. An apparatus according to claim 5 further comprising at least one cylindrical lens mounted between said decollimator and said catadioptric system comprising means for extending the range of said caustic surface curvatures to encompass surfaces which correct for lenticular astigmatism of the eye.

8. The apparatus according to claim 5 wherein of said system is accomplished by a two mirror system where a first mirror comprises means for reflecting the laser beam to a second mirror, said two mirror system functioning to form said caustic surface also having uniform radiation intensity.

9. The apparatus according to claim 5 wherein said catadioptric system is comprised of an axicon lens and a lens structure having front, rear and side-wall optical surfaces, said side-wall optical surface including means for effecting total internal reflection so that all rays entering said front surface are reflected to said rear surface where said rays are refracted to form said desired caustic surface.

10. The apparatus according to claim 5 where said catadioptric system comprises a single thick lens element having front, side-wall, and rear surfaces with an axicon lens surface being the front surface of said element, the side-wall surface of said element including means for effecting total internal reflection of radiation to the rear surface of said element said rear surface comprising means for refracting said radiation to form said caustic surface.

11. The apparatus according to claim 5 wherein a catadioptric system comprising a convex axicon and mirror, where said axicon converges the laser radiation and the converged radiation impinges on said mirror, said mirror having a hole large enough for the material surface to project therethrough, said mirror comprising a means for forming said caustic surface between said axicon lens and said mirror.

12. An apparatus according to claim 5 wherein said decollimator comprises an assemblage of spherical or aspherical lenses having spacing therebetween comprising means for intercepting and decollimating said collimated beam, and means coupled to said lenses for adjusting the spacing between said lenses to produce a continuum of caustic field curves.

13. An apparatus according to claim 5 wherein said catadioptric system is comprised of a concave axicon lens having an optical axis and an aspherical mirror having an optical axis and an external surface, said axicon lens comprising means for diverging the decollimated beam of said decollimator into a cone-shaped pattern of radiation said aspherical mirror comprising means for reflecting said pattern to form said caustic surface.

14. An apparatus according to claim 13 wherein the surface of the aspherical mirror has opaque bands comprising means for monitoring the ablation process.

15. An apparatus according to claim 13 wherein the optical axis of said aspherical mirror is at a 90 degree angle with respect to the optical axis of said axicon lens and a dielectrically coated planar mirror reflecting nearly all the laser radiation but being transparent to visible light is placed at a 45 degree angle to the axis of either the aspherical mirror or axicon comprising means for on axis viewing of the material surface.

16. An apparatus according to claim 5 wherein said source of collimated ablative radiation, said optical device and said corneal surface are all rigidly constrained to a common frame of reference so that said caustic surface may be advanced axially onto the corneal surface without perturbations, said corneal surface being fixed to said frame of reference by a vacuum ring fitted thereon.

17. An apparatus according to claim 16 including an interferometer coupled to a laser firing controller, said interferometer including monitoring means for corneal motion at a rate exceeding the laser pulse rate, said controller comprising means for first said laser only when said corneal surface is within permitted tolerances.

18. An apparatus according to claim 5 wherein said decollimator comprises an assemblage of spherical and aspherical lenses therebetween comprising means for intercepting and decollimating said collimated beam, and means coupled to said lenses for adjusting the spacing between said lenses to produce a continuum of caustic field curvatures.

19. An apparatus according to claim 18 where said decollimator consists of two spherical lenses between which lenses a third lens is mounted, said third lens having at least one aspherical.

20. An apparatus according to claim 5 where said decollimator and said catadioptric system are both contained within an integral housing, said housing being provided with axial adjustment means for positioning said lenses within said decollimator, said housing including means for viewing the material surface, said housing further having an orifice means for supplying air or an inert gas to create a flow of air out of said housing and across said material surface, said housing having attached thereto a cylindrical shield to capture stray radiation.

21. An apparatus according to claim 20 where said axial adjustment means comprises a set of electric servomotor drives each controlling a separate lens within said decollimator.

22. An apparatus according to claim 21 including means coupled to each of each of said drives for controlling each of said drives said means for controlling including a computer, said computer including means for calculating positions of said lenses within said decollimator to produce a particular caustic surface curvature; each of said drives also being equipped with a sensing means for providing feedback to said computer, said sensing means includes means for precisely controlling the positions of said lenses; said computer also including means of material position data from an interferometer means for enabling said computer including means for constraining laser firing only to those instants when the position of the material surface is within permitted tolerances.

23. An apparatus according to claim 13 wherein the surface of the transparent housing has opaque bands comprising means for monitoring the ablation process.

24. An apparatus according to claim 5 wherein said source of collimated, ablative radiation, said optical device, and said corneal surface are all constrained to a common frame of reference so that said caustic surface may be advanced axially onto the corneal surface without perturbations, the apparatus including means for constraining said corneal surface to said frame of reference during firing of the laser, said means for constraining including an interferometer coupled to a laser firing controller, said interferometer including means for monitoring corneal motion at a rate exceeding the pulse rate of the laser, said controller comprising means for firing said laser only when said surface is within permitted tolerances.

* * * * *